United States Patent
Brock-Fisher (10) Patent No.: US 6,213,946 B1
(45) Date of Patent: Apr. 10, 2001

(54) METHODS AND APPARATUS FOR SPECKLE REDUCTION BY ORTHOGONAL PULSE COMPOUNDING IN MEDICAL ULTRASOUND IMAGING

(75) Inventor: George A. Brock-Fisher, Andover, MA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/220,612

(22) Filed: Dec. 24, 1998

(51) Int. Cl.$^7$ .................................................. A61B 8/00
(52) U.S. Cl. ............................................................. 600/443
(58) Field of Search ................................... 600/437, 440, 600/443, 447, 458; 73/625–626; 367/11

(56) References Cited

U.S. PATENT DOCUMENTS

| | | | |
|---|---|---|---|
| Re. 33,672 | 8/1991 | Miwa | 128/660.06 |
| Re. 35,148 | 1/1996 | Lizzi et al. | 348/163 |
| 4,016,750 | 4/1977 | Green | 73/67.5 R |
| 4,446,740 | 5/1984 | Wilson et al. | 73/626 |
| 4,561,019 | 12/1985 | Lizzie et al. | 358/112 |
| 4,569,231 | 2/1986 | Carnes et al. | 73/626 |
| 4,852,577 * | 8/1989 | Smith et al. | 600/443 |
| 4,887,306 | 12/1989 | Hwang et al. | 382/54 |
| 5,000,183 * | 3/1991 | Bonnefous | 73/602 |
| 5,010,885 * | 4/1991 | Fink et al. | 73/625 |
| 5,014,712 * | 5/1991 | O'Donnell | 73/625 |
| 5,129,399 | 7/1992 | Hirama | 128/661.01 |
| 5,187,687 | 2/1993 | Burckhardt et al. | 367/7 |
| 5,255,683 | 10/1993 | Monaghan | 128/662.02 |
| 5,357,962 * | 10/1994 | Green | 73/626 |
| 5,409,007 | 4/1995 | Saunders et al. | 128/661.01 |
| 5,410,516 | 4/1995 | Uhlendorf et al. | 367/74 |
| 5,415,173 * | 5/1995 | Miwa et al. | 600/447 |
| 5,456,257 | 10/1995 | Johnson et al. | 128/662.02 |
| 5,479,926 | 1/1996 | Ustuner et al. | 128/660.04 |
| 5,566,674 | 10/1996 | Weng | 128/660.07 |
| 5,577,505 | 11/1996 | Brock-Fisher et al. | 128/662.02 |
| 5,619,998 * | 4/1997 | Abdel-Malek et al. | 600/443 |
| 5,632,277 | 5/1997 | Chapman et al. | 128/660.07 |
| 5,653,235 | 8/1997 | Teo | 128/661.01 |
| 5,706,819 | 1/1998 | Hwang et al. | 128/662.02 |
| 5,851,187 * | 12/1998 | Thomas, III et al. | 600/447 |
| 5,916,463 * | 10/1999 | Rhyne et al. | 600/458 |
| 5,980,459 * | 11/1999 | Chiao et al. | 600/447 |
| 6,048,315 * | 4/2000 | Chiao et al. | 600/447 |

FOREIGN PATENT DOCUMENTS

0851241A2   1/1988  (EP) .

OTHER PUBLICATIONS

Miller, D.L., "Ultrasonic Detection of Resonant Cavitation Bubbles in a Flow Tube by Their Second–Harmonic Emissions", Ultrasonics, Sep. 1981, pp. 217–224.

(List continued on next page.)

*Primary Examiner*—Francis J. Jaworski (57) ABSTRACT

Speckle artifact is reduced in medical ultrasound images by the use of orthogonal pulse sequences. Ultrasound energy is transmitted into a region of interest in a patient's body, and the transmitted ultrasound energy produces ultrasound echoes from the region of interest. In response to the ultrasound echoes, first and second coherent signals are acquired. The first and second coherent signals correspond to first and second pulse sequences, respectively, which are orthogonal or nearly orthogonal. The first and second coherent signals are combined to provide a composite image signal that is representative of the region of interest. The first and second coherent signals are preferably acquired by first and second matched filters, respectively. The transmitted ultrasound energy may include first and second sequences of ultrasound pulses that correspond to the first and second pulse sequences, respectively.

18 Claims, 5 Drawing Sheets

OTHER PUBLICATIONS

Abbott, John G. et al, "Acoustic Speckle: Theory and Experimental Analysis", Ultrasonic Imaging 1, 1979, pp. 303–324.

Bilgutay, Nihat M. et al, "Spacial Processing for Coherent Noise Reduction in Ultrasonic Imaging", J. Acoust. Soc. Am. 87 (2), Feb., 1990, pp. 728–736.

Trahey, Gregg E. et al, Speckle Pattern Correlation with Lateral Aperture Translation: Experimental Results and Implications for Spatial Compounding, IEEE Trans. on Ultrasonics, Ferroelectrics & Frequency Control, vol. UFCC–33, No. 3, May 1986, pp. 257–264.

Magnin, Paul A. et al, "Frequency Compounding for Speckle Contrast Reduction in Phased Array Images", Ultrasonic Imaging 4, (1982), pp. 267–281.

Entrekin, Robert et al, "Real Time Speckle Reduction in B–Mode Images", 1979 Ultrasonics Symposium, pp. 169–174.

Berger, H. et al, "Ultrasonic Materials Characterization", Proc. of First Int'l. Sym. on Ultrasonic Materials Characterization held at the Nat. Bur. of Standards, Gaithersburg, MD, Jun. 1978, U.S. Dept. of Commerce, Nov., 1980, pp. 550–559.

Bilgutay, N.M. et al, "Flaw Visibility Enhancement by Split–Spectrum Processing Techniques", IEEE Ultrasonics Symposium 1981, pp. 878–883.

Newhouse, V.L. et al, "Flaw–to–Grain Echo Enhancement by Split–Spectrum Processing", Butterworth & Co. (Publishers) Ltd., 1982.

Magnin, Paul A., "A Narrow Bandwidth Multifrequency Ultrasonic Imaging System", Ph.D. Dissertation, Duke University, 1981, pp. 1–144.

Takeuchi, Y., "An Investigation of a Spread Energy Method for Medical Ultrasound Systems" (Part One: Theory and Investigation), IPC Business Press, 1979.

Takeuchi, Y., "An Investigation of a Spread Energy Method for Medical Ultrasound Systems" (Part Two: Proposed System and Possible Problems), IPC Business Press, 1979.

Silverstein, S. D., "Coherence and Speckle Reduction in Compounded Correlated Phased Arrays: Synthetic Aperture Radar", Optical Society of America, vol. 3, No. 11, Nov., 1986, pp. 1925–1934.

* cited by examiner

METHODS AND APPARATUS FOR SPECKLE REDUCTION BY ORTHOGONAL PULSE COMPOUNDING IN MEDICAL ULTRASOUND IMAGING

FIELD OF THE INVENTION

This invention relates to ultrasound imaging systems and, more particularly, to methods and apparatus for producing high quality medical ultrasound images using orthogonal pulse sequences.

BACKGROUND OF THE INVENTION

Ultrasound imaging is widely used in medical applications to non-invasively observe structures within the human body, such as cardiac structures, the vascular system, the fetus, the uterus, the abdominal organs and the eye. In a typical imaging system, short bursts of ultrasound energy are directed into a patient's body with a handheld transducer. The returning reflected energy is received by the same transducer. The signals representing the reflected energy are processed and formatted into a video image of the target region. Phased array scanning techniques are commonly used.

In real-time diagnostic medical ultrasound systems, two-dimensional image quality plays a key role in providing diagnostically significant information for accurate patient diagnosis. However, due to the physical properties governing the generation of an image based on acoustic propagation and reflection of ultrasound energy, state of the art images are affected by various artifacts and degradations. Specifically, clutter and speckle artifacts are observed in the images. Clutter appears as a more or less stationary area of cloudiness formed by small areas of excess, undesired ultrasound energy. Speckle is characterized by small grainy areas where, due to the coherent nature of acoustic image formation, no return signal energy is detected, despite the fact that there is a reflecting medium in the field of view.

Various techniques have been proposed in the prior art for reducing clutter and speckle artifacts in ultrasound images. These approaches generally involve combining images obtained at different times and/or in different frequency bands. See, for example, U.S. Pat. No. Re. 35,148 issued January 23, 1996 to Lizzi et al., which describes a frequency compounding technique. A broadband received signal is applied to separate bandpass filters. The outputs of the filters are detected and summed.

A two-dimensional median filter to reduce speckle artifact in ultrasound imaging is disclosed in U.S. Pat. No. 5,409,007 issued Apr. 25, 1995 to Saunders et al.

A technique for speckle reduction in ultrasound imaging using a two-dimensional array of transducer elements is disclosed in U.S. Pat. No. 5,653,235 issued Aug. 5, 1997 to Teo.

Spatial compounding is another prior art technique for reducing speckle in ultrasound images. In spatial compounding, an object is imaged from two or more points in space, and the resulting images are combined to form a single image. If the points in space are sufficiently distant from one another, the speckle patterns produced are not correlated with each other.

Prior art techniques for reducing clutter and speckle artifacts have exhibited limited improvement in image quality. Accordingly, there is a need for additional techniques for enhancing image quality, which may be used separately or in combination with known techniques.

SUMMARY OF THE INVENTION

According to a first aspect of the invention, a method is provided for generating a medical ultrasound image. The method comprises the steps of transmitting ultrasound energy into a region of interest in a patient's body, the transmitted ultrasound energy producing ultrasound echoes from the region of interest, and acquiring, in response to the ultrasound echoes, first and second coherent signals that correspond to first and second pulse sequences, respectively. The second pulse sequence is orthogonal or nearly orthogonal to the first pulse sequence. The method further comprises combining the first and second coherent signals to provide a composite image signal that is representative of the region of interest.

In a first embodiment, the step of transmitting ultrasound energy comprises transmitting first and second sequences of ultrasound pulses at different times. The first and second sequences of ultrasound pulses correspond to the first and second pulse sequences, respectively.

In a second embodiment, a combined sequence of ultrasound pulses containing ultrasound pulses corresponding to the first and second pulse sequences is transmitted.

In a third embodiment, an ultrasound pulse having a pulse duration at least as long as the first and second pulse sequences is transmitted.

In the above embodiments, the step of acquiring a first coherent signal may include selecting the first coherent signal with a first matched filter having a characteristic matched to the first pulse sequence, and the step of acquiring a second coherent signal may include the step of selecting the second coherent signal with a second matched filter having a characteristic matched to the second pulse sequence.

In one example, the step of combining the first and second coherent signals may include processing the first and second coherent signals to remove phase information and form first and second noncoherent signals, respectively, and summing the first and second noncoherent signals. In another example, the step of combining the first and second coherent signals may include summing the first and second coherent signals to form a combined signal and processing the combined signal to remove phase information and form a noncoherent signal.

The steps of transmitting the first and second sequences of ultrasound pulses may comprise varying one or more parameters of the first and second sequences of ultrasound pulses during image data acquisition.

According to a further aspect of the invention, apparatus is provided for generating a medical ultrasound image. The apparatus comprises an ultrasound transducer, an ultrasound transmitter for transmitting ultrasound energy into a region of interest in a patient's body with the ultrasound transducer, the transmitted ultrasound energy producing ultrasound echoes from the region of interest, a receive beamformer for generating a beamformer signal representative of a receive beam in response to the ultrasound echoes, and a signal processor. The signal processor comprises first and second matched filters for acquiring first and second coherent signals, respectively, in response to the beamformer signal and a combining unit for combining the first and second coherent signals to provide a composite image signal that is representative of the region of interest. The first and second matched filters have characteristics that are matched to the first and second pulse sequences, respectively. The second pulse sequence is orthogonal or nearly orthogonal to the first pulse sequence.

According to another aspect of the invention, methods and apparatus are provided for generating an ultrasound image. An ultrasound transmitter transmits a first sequence of ultrasound pulses and a second sequence of ultrasound pulses into a region of interest in a patient's body with the ultrasound transducer. The transmitted ultrasound energy produces ultrasound echoes from the region of interest. The second sequence of ultrasound pulses is orthogonal or nearly orthogonal to the first sequence of ultrasound pulses. An ultrasound receiver acquires, in response to the ultrasound echoes, first and second coherent signals that correspond to the first and second sequences of ultrasound pulses, respectively, and combines the first and second coherent signals to provide a composite image signal that is representative of the region of interest.

BRIEF DESCRIPTION OF THE DRAWINGS

For a better understanding of the present invention, reference is made to the accompanying drawings, which are incorporated herein by reference and in which.

DETAILED DESCRIPTION

Figure 1:
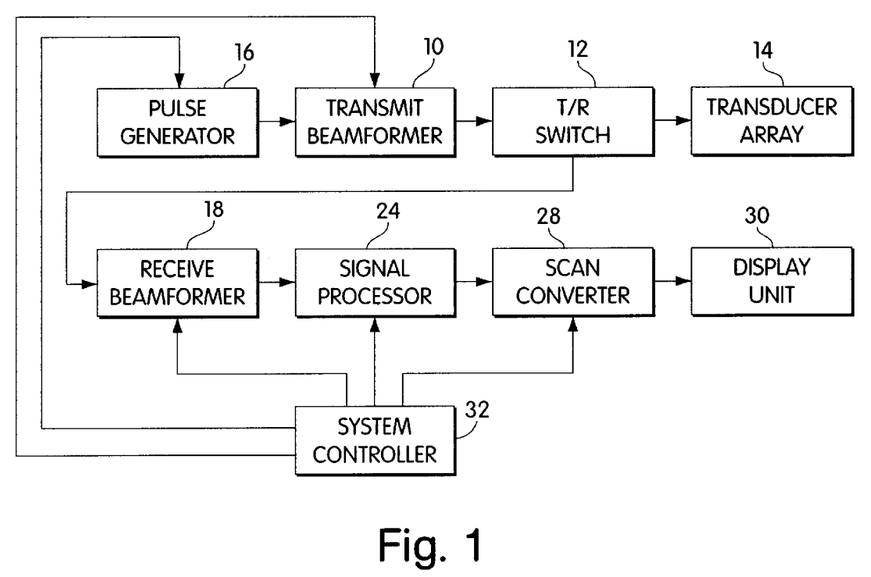
FIG. 1 is a block diagram of an example of an ultrasound imaging system incorporating the present invention.

A simplified block diagram of an example of an ultrasound imaging system incorporating the present invention is shown in FIG. 1. A transmit beamformer 10 is coupled through a transmit/receive (T/R) switch 12 to a transducer array 14, which includes an array of transducer elements. The T/R switch 12 typically has one switch element for each transducer element. The transmit beamformer 10 receives transmit pulse sequences from a pulse generator 16.

The transducer array 14, energized by the transmit beamformer, transmits ultrasound energy into a region of interest in a patient's body and receives reflected ultrasound energy, or echoes, from various structures and organs within the patient's body. As is known in the art, by appropriately delaying the pulses applied to each transducer element by transmit beamformer 10, a focused ultrasound beam is transmitted along a desired scan line.

The transducer array 14 is coupled through T/R switch 12 to a receive beamformer 18. Ultrasound energy from a given point within the patient's body is received by the transducer elements at different times. The transducer elements convert the received ultrasound energy to transducer signals which may be amplified, individually delayed and then summed by receive beamformer 18 to provide a beamformer signal that represents the received ultrasound level along a desired receive line. A digital beamformer may include an analog-to-digital converter for converting the transducer signals to digital values. As known in the art, the delays applied to the transducer signals may be varied during reception of ultrasound energy to effect dynamic focussing. The process is repeated for multiple scan lines to provide signals for generating an image of the region of interest in the patient's body. The receive beamformer 18 may, for example, be a digital beamformer of the type used in the HP Sonos 5500 ultrasound system manufactured and sold by Hewlett-Packard Company.

The scan pattern may be a sector scan, wherein scan lines typically originate at the center of the transducer array 14 and are directed at different angles. Linear, curvilinear and other scan patterns may also be utilized. Furthermore, the scan pattern may be two-dimensional or three-dimensional. In an alternative system configuration, different transducer elements are used for transmit and receive. In that configuration, the T/R switch is not required, and the transmit beamformer 10 and the receive beamformer 18 are connected directly to the respective transmit and receive transducer elements. The beamformer signals are applied to a signal processor 24 which processes the beamformer signal for improved image quality as described in detail below. Receive beamformer 18 and signal processor 24 constitute an ultrasound receiver. The output of signal processor 24 is supplied to a scan converter 28 which converts sector scan or other scan pattern signals to conventional raster scan display signals. The output of scan converter 28 is supplied to a display unit 30, which displays an image of the region of interest in the patient's body. In the case of a three-dimensional scan pattern, the scan converter 28 may be replaced by an image data buffer that stores the three-dimensional data set and a processor that converts the three-dimensional data set to a desired two-dimensional image. A system controller 32 provides overall control of the system. The system controller 32 performs timing and control functions and typically includes a microprocessor and associated memory.

In accordance with a feature of the invention, speckle artifact in ultrasound images is reduced by utilizing orthogonal or nearly orthogonal pulse sequences to provide decorrelated signals from multiple scatterers. The technique involves the use of two or more pulse sequences that are mathematically orthogonal or nearly orthogonal. Two pulse sequences are mathematically orthogonal when the product of the two pulse sequences integrated over time is zero. The pulse sequences are pulses of ultrasound energy at the ultrasound frequency. Thus, orthogonality is affected by pulse amplitude, pulse timing, ultrasound frequency and ultrasound phase. The two pulse sequences may be nearly orthogonal if the result of the above operation is a small, nonzero value. The received signals corresponding to the orthogonal pulse sequences are processed separately and then are combined to form a composite image signal having low speckle artifact.

Figure 2:
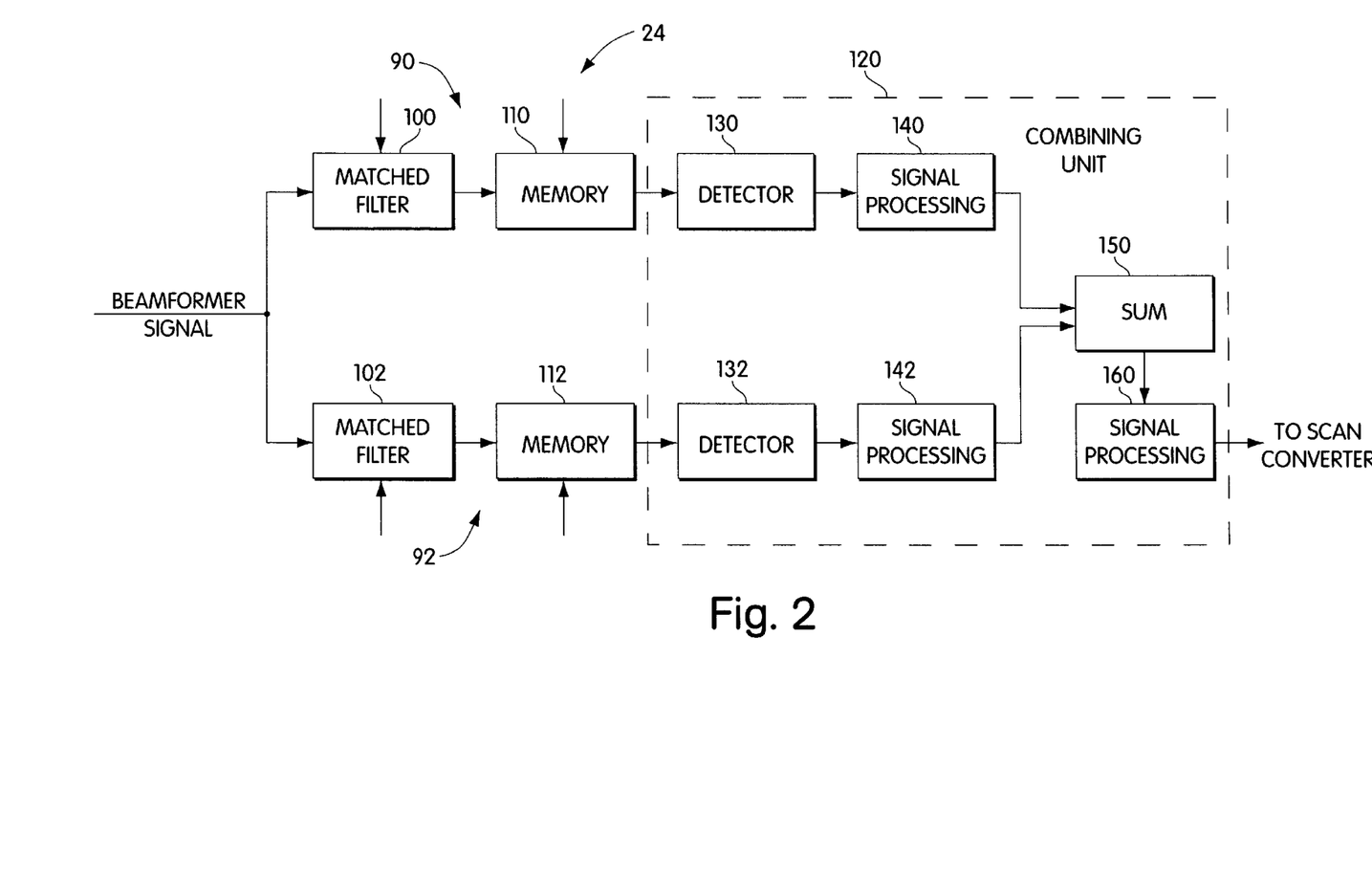
FIG. 2 is a block diagram of a first example of the signal processor shown in FIG. 1.

A block diagram of a first example of signal processor 24 (FIG. 1) is shown in FIG. 2. Signal processor 24 includes parallel processing channels 90 and 92. The beamformer signal from receive beamformer 18 is supplied in parallel to a matched filter 100 and a matched filter 102. Each of the matched filters 100 and 102 is matched to one of the orthogonal pulses sequences. As known in the art, a matched filter is configured to select a predetermined pulse sequence from a received signal. Matched filters 100 and 102 may be programmable under control of system controller 32 (FIG. 1) to permit use of different orthogonal pulse sequences. Matched filters 100 and 102 provide coherent image signals representative of the received ultrasound echoes and corresponding to the respective pulse sequences. Coherent signals refer to those that contain phase information regarding the received signals.

The outputs of matched filters 100 and 102 are stored in memories 110 and 112, respectively. The data corresponding to each pulse sequence is stored in the respective memory as data is acquired. Thus, memories 110 and 112 contain image data representative of the same image space and corresponding to the respective pulse sequences. The outputs of memories 110 and 112 are supplied to a combining unit 120 which combines the coherent data values corresponding to each spatial point in the image space to provide a composite image signal that is representative of the region of interest. The composite image signal is supplied to scan converter 28 (FIG. 1).

In the example of FIG. 2, combining unit 120 includes a detector 130 coupled to the output of memory 110 and a detector 132 coupled to the output of memory 112. The detectors 130 and 132 remove phase information from the respective coherent image data stored in memories 110 and 112 and form noncoherent image data. The noncoherent image data supplied by detectors 130 and 132 may be subjected to additional signal processing, such as for example lowpass filtering and/or logarithmic compression, in signal processing blocks 140 and 142, respectively. When additional signal processing is not required, signal processing blocks 140 and 142 may be omitted from combining unit 120.

The outputs of processing blocks 140 and 142 are supplied to a summing unit 150, which adds or averages the noncoherent image data. The output of summing unit 150 may be subjected to additional signal processing, such as for example lowpass filtering and/or logarithmic compression, in a signal processing block 160. The output of combining unit 120 is composite image data which is enhanced in image quality in comparison with the image data in each processing channel and in comparison with image data that is acquired without the use of orthogonal pulse compounding. Referring again to FIG. 2, processing channel 90 includes matched filter 100, memory 110, detector 130, and signal processing block 140; and processing channel 92 includes matched filter 102, memory 112, detector 132, and signal processing block 142.

Detectors 130 and 132 may be quadrature detectors, amplitude envelope detectors or any other suitable detectors. The log compression operation compresses the dynamic range of the input signal. Log compression may be performed following summing unit 150 or may be performed in each processing channel prior to summing unit 150.

Memories 110 and 112 may have sufficient capacity to store image data for a complete two-dimensional ultrasound image. Different techniques may be used for writing data into memory and reading data from memory. In general, coherent image data is written into each memory as it is acquired from the region of interest by the imaging system. Reading of data from memories 110 and 112 depends on the format of the pulse sequence utilized. In general, image data for a spatial image point must be available in both channels before it can be read from memory and combined. In one approach, image data for an entire image or for a single receive line of an image is acquired and is written into memories 110 and 112 before reading and combining of the image data. In another approach, image data is read from the memories 110 and 112 as soon as data values for a selected spatial image point are available. To provide maximum flexibility, dual port memories, which permit simultaneous writing and reading, may be utilized.

Figure 2A:
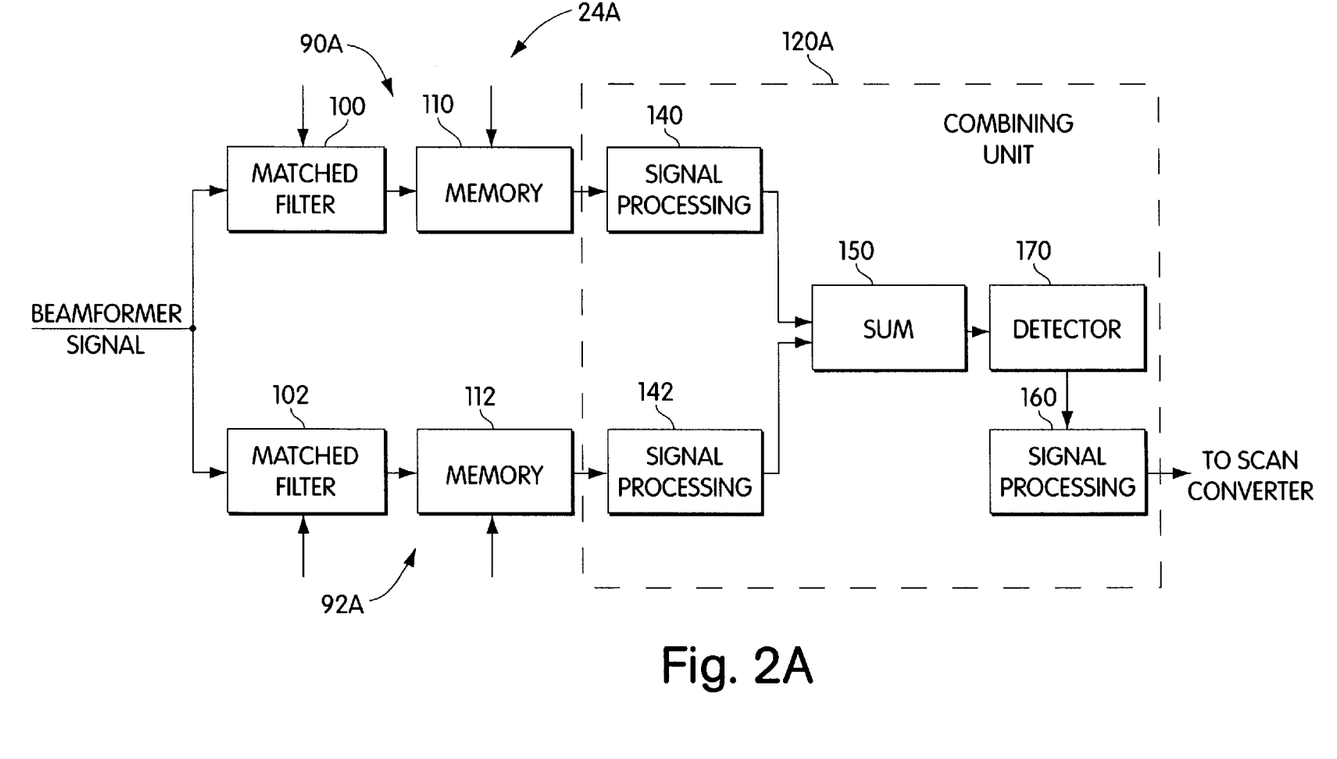
FIG. 2A is a block diagram of a second example of the signal processor shown in FIG. 1.

A block diagram of a second example of the signal processor 24 is shown in FIG. 2A. A signal processor 24A includes parallel processing channels 90A and 92A. Like elements in FIGS. 2 and 2A have the same reference numerals. In the example of FIG. 2A, a combining unit 120A includes signal processing block 140 coupled to the output of memory 110 and signal processing block 142 coupled to the output of memory 112. As noted above, signal processing blocks 140 and 142 may perform signal processing functions such as lowpass filtering and/or logarithmic compression. The coherent image data output by signal processing blocks 140 and 142 are supplied to summing unit 150, which adds or averages the coherent image data to provide a combined signal. The output of summing unit 150 is supplied to a detector 170 which removes phase information from the combined signal at the output of summing unit 150 and forms noncoherent image data. The output of detector 170 may be subjected to additional signal processing, such as, for example, lowpass filtering and/or logarithimic compression, in signal processing block 160. The output of combining unit 120A is composite image data which is enhanced in image quality in comparison with the image data in each processing channel and in comparison with image data that is acquired without the use of orthogonal pulse compounding. Processing channel 90A includes matched filter 100, memory 110, and signal processing block 140; and processing channel 92A includes matched filter 102, memory 112, and signal processing block 142.

Figure 3:
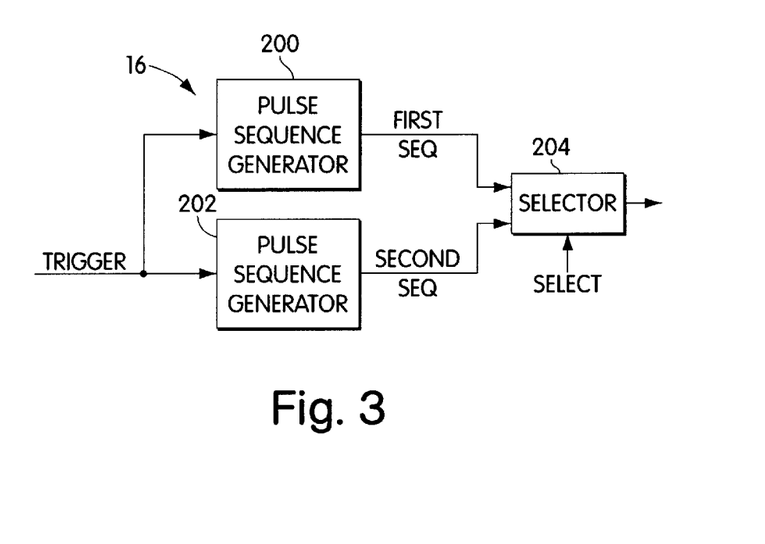
FIG. 3 is a block diagram of an example of the pulse generator shown in FIG. 1.

A first embodiment of the invention is described with reference to FIGS. 1–4. As shown in FIG. 3, pulse generator 16 may include a pulse sequence generator 200 and a pulse sequence generator 202. Pulse sequence generators 200 and 202 receive a trigger pulse from system controller 32 (FIG. 1) and supply outputs to a data selector 204. Data selector 204 receives a select signal from system controller 32. Depending on the state of the select signal, data selector 204 provides the output of pulse sequence generator 200 or pulse sequence generator 202.

Figure 4:
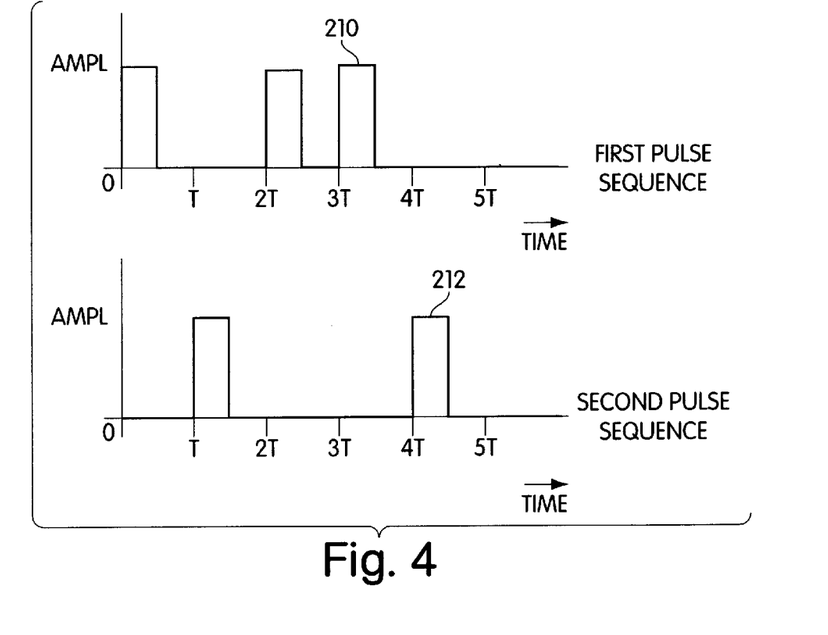
FIG. 4 is a graph of voltage as a function of time, showing an example of orthogonal pulse sequences in accordance with a first embodiment of the invention.

As shown in FIG. 4, pulse sequence generator 200 generates a first pulse sequence 210, and pulse sequence generator 202 supplies a second pulse sequence 212. The pulse sequences 210 and 212 have time durations 5T, where T is the time duration of a single bit, or pulse, of the pulse sequence. The pulse sequences 210 and 212 are orthogonal. The orthogonality may be understood with respect to pulse sequences 210 and 212 by observing that the amplitude of one of the two pulse sequences is zero at each instant of time between time t=0 and time t=5T. Thus, the product of the pulse sequences integrated from time t=0 to time t=5T is zero.

In general, the time duration of the pulse sequence is short in comparison with the time for acquiring image data from the patient's body. Typically, the time duration of the pulse sequence is less than 32 cycles of the ultrasound frequency. Sequences of coded pulses, such as Golay codes, suitable for use in medical ultrasound systems are described by Y. Takeuchi in "An Investigation of a Spread Energy Method for Medical Ultrasound Systems, Part One: Theory and Investigation", Ultrasonics, July 1979, and in "An Investigation of a Spread Energy Method for Medical Ultrasound Systems, Part Two: Proposed System and Possible Problems", Ultrasonics, September, 1979. Suitable pulse sequences for medical ultrasound imaging typically have a length between about 3 and 16 bits. As indicated above, the pulse sequences may have any combination of timing, amplitudes, phases and frequencies which result in orthogonality or near orthogonality.

Referring again to FIGS. 1–4, first pulse sequence 210 is selected by selector 204 and is output to transmit beamformer 10 (FIG. 1) to produce a first transmit event. The transmit beamformer 10 delays the pulses supplied to the transducer elements of the array 14 to steer and focus the transmitted ultrasound energy along a desired transmit line. The received ultrasound echoes are processed by receive beamformer 18, and the beamformer signal is supplied to signal processor 24. Matched filter 100 (FIG. 2) recognizes first pulse sequence 210 and supplies the corresponding image data to memory 110. In a second transmit event, data selector 204 selects the second pulse sequence 212 output by pulse sequence generator 202 and supplies the selected pulse sequence to transmit beamformer 10. Transmit beamformer 10 steers and focuses the transmitted ultrasound energy along the same transmit line. The receive beamformer 18 processes the received ultrasound echoes and supplies a beamformer signal to signal processor 24. Matched filter 102 recognizes the second pulse sequence and stores the corresponding image data in memory 112. This process is repeated for each transmit line in the scan pattern, and the corresponding image data is stored in memories 110 and 112. In this example of a scan protocol, the first and second pulse sequences are transmitted on an alternating basis for each transmit line in the scan pattern.

After the image data is stored in memories 110 and 112, reading of image data may proceed. The coherent image data for corresponding image points is read from memories 110 and 112. The coherent image data is processed by detectors 130 and 132 to remove phase information and form noncoherent image data. The noncoherent image data is processed, if necessary, in blocks 140 and 142. The noncoherent image data is then summed by summing unit 150. The combined image data is processed, if necessary, in processing block 160 to form composite image data. The composite image data is supplied to scan converter 28.

In an alternate of the above scan protocol, the first pulse sequence 210 may be utilized to acquire image data for the entire image. Then the second pulse sequence 212 is utilized to acquire image data for the entire image. Reading of image data from memories 110 and 112 may proceed after two complete scans of the image space.

Figure 5:
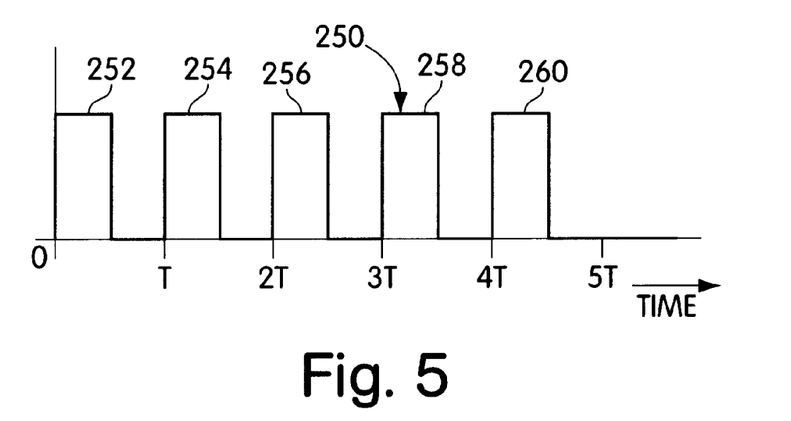
FIG. 5 is a graph of voltage as a function of time, showing an example of a combined pulse sequence in accordance with a second embodiment of the invention.

A second embodiment of the invention is described with reference to FIGS. 1, 2 and 5. In the embodiment of FIG. 5, pulse generator 16 generates a combined pulse sequence that contains first and second orthogonal pulse sequences, and the orthogonal pulse sequences are transmitted concurrently. Thus, a combined pulse sequence containing a first pulse sequence and a second pulse sequence, wherein the first and second pulse sequences are mathematically orthogonal, is transmitted. The combined pulse sequence may be generated by adding the first and second pulse sequences or by directly generating the combined pulse sequence. Referring to FIG. 5, a combined pulse sequence 250 is formed by adding the pulse sequences 210 and 212 shown in FIG. 4. In combined pulse sequence 250, pulses 252, 256 and 258 correspond to pulse sequence 210, and pulses 254 and 260 correspond to pulse sequence 212.

The operation of the second embodiment is the same as that described above in connection with FIG. 4, except that the matched filters 100 and 102 select the first and second pulse sequences from the beamformer signal concurrently. For each combined pulse sequence, image data corresponding to the first pulse sequence is stored in memory 110, and image data corresponding to the second pulse sequence is stored in memory 112. The image data may be processed by combining unit 120 as described above in connection with the first embodiment. The second embodiment has the advantage that both pulse sequences are transmitted concurrently, thereby avoiding any decrease in frame rate.

Figure 6:
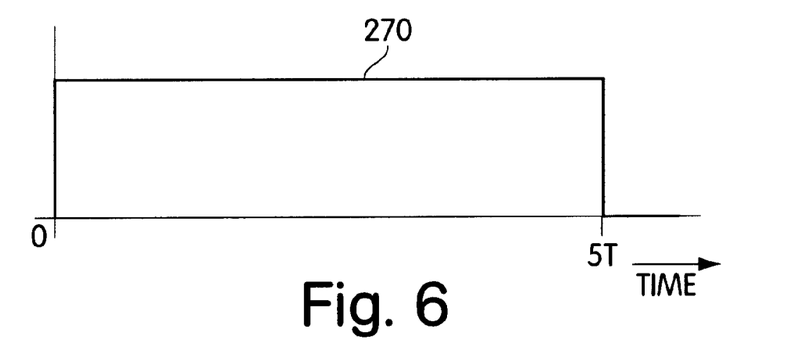
FIG. 6 is a graph of voltage as a function of time, showing an example of a single transmitted pulse in accordance with a third embodiment of the invention.

A third embodiment of the invention is described with reference to FIGS. 1, 2 and 6. In this embodiment, pulse generator 16 generates a single transmit pulse 270 having a duration ST that corresponds to the time duration of orthogonal pulse sequences that are preprogrammed into matched filters 100 and 102. In signal processor 24, matched filters 100 and 102 concurrently select received signals in time intervals corresponding to first and second orthogonal or nearly orthogonal pulse sequences. For each transmit pulse 270, image data corresponding to the first pulse sequence is stored in memory 110, and image data corresponding to the second pulse sequence is stored in memory 112. The image data may be processed by the combining unit 120 as described above in connection with the first embodiment. As in the embodiment of FIG. 5, image data for the first and second pulse sequences is acquired concurrently. The embodiment of FIG. 6 has the advantages, as compared with the embodiment of FIG. 4, of increased frame rate and, as compared with the embodiments FIGS. 4 and 5, of not requiring transmit pulse sequences.

In each of the embodiments described above, signal processor 24 includes matched filters 100 and 102, which are respectively matched to orthogonal pulse sequences. Because the image data corresponding to the orthogonal pulse sequences is decorrelated with respect to speckle, image quality is improved when the separate image data sets are detected and combined.

The invention has been described thus far in connection with use of two or more orthogonal pulse sequences. As described above, the pulse sequences are mathematically orthogonal when the product of the pulse sequences integrated over the time duration of the pulse sequences is zero. The condition where the pulse sequences are truly orthogonal provides best image quality. However, it will be understood that improved image quality may be obtained where the pulse sequences are nearly orthogonal, i.e. where the integral over time is a small, nonzero value. It will further be understood that the image quality is gradually degraded as the departure from true orthogonality decreases. Thus, nearly orthogonal pulse sequences may be utilized where some degradation in image quality is acceptable.

In accordance with a further feature of the invention, one or more parameters of the transmit pulse sequences may be varied during image data acquisition. For example, the parameters of the pulse sequences may be varied as a function of transmit angle or image depth. By way of example, it may be desirable to decrease the ultrasound transmit frequency as the transmit angle relative to a direction normal to the transducer increases. In this instance, it may be desirable to increase the width of the transmit pulses and the length of the pulse sequences as the transmit angle increases.

It will be understood that the embodiments shown and described above are given by way of example only and are not limiting as to the scope of the present invention. For example, the orthogonal pulse sequences utilized to obtain enhanced image quality may have different numbers of pulses, or bits, different pulse shapes, different pulse widths, different amplitudes, different frequencies, different phases and the like, provided that the pulse sequences are orthogonal or nearly orthogonal. Furthermore, the invention may be implemented in a variety of different ultrasound imaging system configurations. Both digital and analog implementations may be utilized. Furthermore, the combining unit 120 shown in FIG. 2 and described above may have a variety of different configurations within the scope of the invention. The invention may be used separately or in combination with other techniques for reducing speckle artifact and enhancing image quality. The invention may be used when contrast agents are in use.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A method for generating a medical ultrasound image, comprising the steps of:

transmitting first and second pulse sequences of ultrasound energy into a region of interest in a patient's body, the first sequence being orthogonal or nearly orthogonal to the second pulse sequence;

acquiring a first coherent signal in response to ultrasound echoes with a first matched filter having a characteristic that is matched to the first pulse sequence;

acquiring a second coherent signal in response to the ultrasound echoes with a second matched filter having a characteristic that is matched to the second pulse sequence; and combining the first and second coherent signals to provide a composite image signal that is representative of the region of interest.

2. A method for generating a medical ultrasound image as defined in claim 1 wherein the first and second pulse sequences are transmitted as a combined sequence of ultrasound pulses that contains ultrasound pulses corresponding to said first and second pulse sequences.

3. A method for generating a medical ultrasound image as defined in claim 1 wherein the first and second pulse sequences are transmitted as a single pulse having a pulse duration that is at least as long as said first and second pulse sequences.

4. A method for generating a medical ultrasound image as defined in claim 1 wherein the step of combining the first and second coherent signals comprises processing the first and second coherent signals to remove phase information thereby forming first and second noncoherent signals, respectively, and summing the first and second noncoherent signals.

5. A method for generating a medical ultrasound image as defined in claim 1 wherein the step of combining the first and second coherent signals comprises summing the first and second coherent signals to form a combined signal, and processing the combined signal to remove phase information and form a noncoherent signal.

6. Apparatus for generating a medical ultrasound image, comprising:

an ultrasound transducer;

an ultrasound transmitter for transmitting first and second pulse sequences of ultrasound energy into a region of interest in a patient's body, the first sequence being orthogonal being orthogonal or nearly orthogonal to the second pulse sequence;

a receive beamformer for generating a beamformer signal representative of a receive beam in response to ultrasound echoes; and a signal processor comprising:

a first matched filter for acquiring a first coherent signal in response to the beamformer signal, the first matched filter having a characteristic that is matched to the first pulse sequence;

a second matched filter for acquiring a second coherent signal in response to the beamformer signal, the second matched filter having a characteristic that is matched to the second pulse sequence; and a combining unit for combining the first and second coherent signals to provide a composite image signal that is representative of the region of interest.

7. Apparatus as defined in claim 6 wherein the first and second ultrasound pulses are transmitted as a combined sequence of ultrasound pulses that contains ultrasound pulses corresponding to the first and second pulse sequences.

8. Apparatus as defined in claim 6 wherein the first and second ultrasound pulses are transmitted as an ultrasound pulse having a pulse duration that is at least as long as the first and second pulse sequences.

9. Apparatus as defined in claim 6 wherein signal processor further comprises a first memory coupled to an output of the first matched filter for storing the first coherent signal and a second memory coupled to an output of the second matched filter for storing the second coherent signal.

10. Apparatus as defined in claim 6 wherein the combining unit comprises a processor for processing the first and second coherent signals to remove phase information and form first and second noncoherent signals, respectively, and a summing unit for summing the first and second noncoherent signals.

11. Apparatus as defined in claim 6 wherein the combining unit comprises a summing unit for summing the first and second coherent signals to form a combined signal, and a processor for processing the combined signal to remove phase information and form a noncoherent signal.

12. A method for generating a medical ultrasound image, comprising the steps of:

transmitting first and second sequences of ultrasound pulses into a region of interest in a patient's body, the transmitted ultrasound energy producing ultrasound echoes from the region of interest, the second sequence of ultrasound pulses being orthogonal or nearly orthogonal to the first sequence of ultrasound pulses;

in response to the ultrasound echoes, selecting a first coherent signal with a first matched filter having a characteristic matched to the first sequence of ultrasound pulses and selecting a second coherent signal with a second matched filter having a characteristic matched to the second sequence of ultrasound pulses; and combining the first and second coherent signals to provide a composite image signal that is representative of the region of interest.

13. A method for generating a medical ultrasound image as defined in claim 12 further comprising the step of storing the first and second coherent signals.

14. A method for generating a medical ultrasound image comprising the steps of:

combining first and second sequences of ultrasound pulses to form a third sequence of ultrasound pulses, the second sequence of ultrasound pulses being orthogonal or nearly orthogonal to the first sequence of ultrasound pulses;

transmitting the third sequence of ultrasound pulses into a region of interest in a patient's body, the transmitted ultrasound energy producing ultrasound echoes from the region of interest;

acquiring, in response to the ultrasound echoes, first and second coherent signals that correspond to the first and second sequences of ultrasound pulses, respectively; and combining the first and second coherent signals to provide a composite image signal that is representative of the region of interest.

15. A method for generating a medical ultrasound image as defined in claim 14 wherein the step of acquiring first and second coherent signals comprises selecting the first coherent signal with a first matched filter having a characteristic that is matched to the first sequence of ultrasound pulses, and selecting the second coherent signal with a second matched filter having a characteristic that is matched to the second sequence of ultrasound pulses.

16. A method for generating a medical ultrasound image as defined in claim 12 wherein the step of transmitting first and second sequences of ultrasound pulses comprises varying one or more parameters of the first and second sequences of ultrasound pulses during image data acquisition.

17. A method for generating a medical ultrasound image comprising the steps of:

transmitting first and second sequences of ultrasound pulses into a region of interest in a patient's body, the transmitted ultrasound energy producing ultrasound echoes from the region of interest, the second sequence of ultrasound pulses being orthogonal or nearly orthogonal to the first sequence of ultrasound pulses;

acquiring, in response to the ultrasound echoes, first and second coherent signals that correspond to the first and second sequences of ultrasound pulses, respectively; and processing the first and second coherent signals to remove phase information and form first and second noncoherent signals, respectively, and summing the first and second noncoherent signals so as to provide a composite image signal that is representative of the region of interest.

18. A method for generating a medical ultrasound image comprising the steps of:

transmitting first and second sequences of ultrasound pulses into a region of interest in a patient's body, the transmitted ultrasound energy producing ultrasound echoes from the region of interest, the second sequence of ultrasound pulses being orthogonal or nearly orthogonal to the first sequence of ultrasound pulses;

acquiring, in response to the ultrasound echoes, first and second coherent signals that correspond to the first and second sequences of ultrasound pulses, respectively; and summing the first and second coherent signals to form a combined signal, and processing the combined signal to remove phase information and form a noncoherent signal so as to provide a composite image signal that is representative of the region of interest.

* * * * *